United States Patent [19]

Gore et al.

[11] Patent Number: 4,620,605

[45] Date of Patent: Nov. 4, 1986

[54] SUSPENSION FOR ELECTRO-ACOUSTICAL TRANSDUCERS

[76] Inventors: Gordon B. Gore, 15 McArdle Rd., Ermington, New South Wales 2115; Malcolm J. Clark, 3 Lebanon St., Dandenong, Victoria 3175; John R. Le Strange, 2 Francis St., Strathfield West, New South Wales 2140, all of Australia

[21] Appl. No.: 776,143

[22] PCT Filed: Jan. 3, 1985

[86] PCT No.: PCT/AU85/00001

§ 371 Date: Oct. 3, 1985

§ 102(e) Date: Oct. 3, 1985

[87] PCT Pub. No.: WO85/03185

PCT Pub. Date: Jul. 18, 1985

[51] Int. Cl.[4] ............................................ A61B 7/02

[52] U.S. Cl. ................................ 181/135; 181/130; 181/158; 181/171; 381/68.6; 381/187

[58] Field of Search ............... 181/135, 157, 158, 130, 181/171, 172; 179/146 E, 179, 180, 184, 107 E, 107 H

[56] References Cited

U.S. PATENT DOCUMENTS 2,430,229 11/1947 Kelsey ............................ 179/182 R 3,448,224 6/1969 Giller ............................. 179/107 E

*Primary Examiner*—Benjamin R. Fuller

*Attorney, Agent, or Firm*—Harness, Dickey & Pierce

[57] ABSTRACT

A moulded suspension for an electro-acoustic transducer in the form of a microphone or a receiver has three regions. A transducer supporting region fits closely around the transducer. A tubular inlet region connects the acoustical inlet or outlet of the transducer to a respective port of the appliance containing the transducer. The third region is a tubular foot which has an annular flange so that the moulding can be mounted adjacent to an aperture formed in a supporting plate. The suspension is made of an elastomeric material. It provides a high degree of vibration isolation and is particularly suitable for use in "behind-the-ear" hearing aids.

6 Claims, 8 Drawing Figures

SUSPENSION FOR ELECTRO-ACOUSTICAL TRANSDUCERS

TECHNICAL FIELD

This invention concerns mounting systems for electro-acoustical transducers. It is particularly applicable to the mounting of small transducers in small electro-acoustical appliances, such as portable tape recorders and dictaphones, hand-held portable transceivers and hearing aids (including "behind the ear" and "in the ear" hearing aids). However, the invention is not limited to such applications alone. For example, it can be used with advantage in head-mounted transceivers of the type commonly used by aircraft pilots.

BACKGROUND ART

In general terms, microphones are devices which convert, or transduce, acoustical energy into electrical energy. It is well known that microphones which use a moving diaphragm are sensitive to vibration caused by shocks or movement, and that when microphones are subjected to forces causing vibration, they produce an unwanted signal. The sensitivity to vibration is a function of design, and thus varies according to the type of microphone.

Receivers (sometimes called "speakers" or alternatively "earphones", according to the context in which the term is used) are devices which transduce electrical energy into acoustical energy. Their construction includes a motor and diaphragm system which is driven by an electrical input signal. When in operation, the motor and diaphragm system produce out-of-balance forces in the form of structure-transmitted vibration.

Appliances such as hearing aids (which use a microphone and receiver simultaneously), small tape recorders (which contain microphones and sometimes receivers) and hand-held transceivers (which alternately use a microphone and a receiver) require their transducers to be protected against unwanted structure-borne forces.

It is known that the sensitivity of these transducers (microphones and receivers) to the reception or transmission of vibration or shock energy is always a maximum when the forces which cause the unwanted movement are applied in a direction normal to the plane of the diaphragm of the transducer. The function of a transducer mounting, therefore, is to locate the transducer within a defined space and to isolate it as much as possible from the reception or transmission of unwanted structure-borne vibrational forces.

The usual transducer mounting system used in hearing aids and other small electro-acoustical appliances comprises a short length of hollow resilient tubing (which transmits acoustical energy to the transducer in the case of a microphone or from the transducer in the case of a receiver) together with at least one buffer which is remote from the acoustic input or output of the transducer. The buffer or buffers are usually loose fitting and act in compression when in contact with the walls enclosing the defined space. The effectiveness of the vibrational isolating properties of this design of suspension depends largely on the compliance and damping properties of the material that is used to manufacture the tubing and the buffers. A high compliance is always sought so that the resonance frequency of the suspension system is both low and away from the operating frequency range of the appliance. A high degree of damping is also sought to minimise direct transmission of energy through the suspension points. These material characteristics are difficult to obtain in practice and always place stringent constraints on manufacturing procedures. Despite this knowledge of the required characteristics of suspension systems, these systems remain a compromise solution in practice.

DISCLOSURE OF THE PRESENT INVENTION

It is an object of the present invention to provide a new form of suspension or mounting system for small electro-acoustical transducers which is simple to put into practice, is economical to produce, and is more effective than the suspensions which are currently available because it achieves a higher compliance and therefore has a lower resonance frequency than existing systems.

This objective is achieved by providing a moulding of soft rubber or similar material which has two ends and which is formed to be a close, substantially encapsulating, fit over the transducer. This moulding is designed to deform largely in shear. One of the ends of the moulding is tubular and is adapted to extend from the inlet or outlet port of the transducer to the acoustical inlet or outlet of the appliance in which the transducer is mounted, and to be supported by the appliance acoustical inlet or outlet port or a tube extending therefrom. The other end of the moulding (which is also tubular but may be perforated and could be of a web construction) is provided with an annular flange so that it may be mounted, in a manner similar to that in which a grommet is mounted, on a supporting plate or the like having an aperture therein.

When using this moulding, a transducer is suspended between two fixed points by a relatively thin elastomer material. Wires that have to be connected to the transducer can conveniently be passed through the end of the moulding which is provided with a flange, to simplify the construction of the appliance.

Thus, according to one form of the present invention, there is provided a mounting suspension for an electro-acoustical transducer to be supported in a predetermined location relative to an acoustic input or output of an appliance, said suspension comprising a moulding of soft rubber or similar elastomeric material, said moulding being characterised in that it comprises (a) a transducer-supporting region having a shape which corresponds to the external shape of the transducer, said transducer supporting region being adapted to be a tight fit around the transducer;

(b) a tubular region, extending from said transducer-supporting region, the end portion of said tubular region which is remote from the transducer-supporting region being close fitting over, and supportable by, the end region of a rigid extending from the acoustic input or output of the appliance, said tubular region having an end portion closest to the transducer supporting region which is close fitting over said acoustical inlet or tubular projection of the transducer when the transducer is located within the transducer-supporting region and the suspension is incorporated into the appliance; and (c) a tubular foot, extending from the end of the transducer-supporting region which is remote from said tubular region, said tubular foot including an annular flange extending radially from the axis of the tubular foot, said flange being adapted to retain the tubular foot in a position in which the tubular foot extends through an aperture formed in a mounting plate of the appliance.

An embodiment of the present invention in its (non-limiting) application to hearing aids, will now be described, with reference to the accompanying drawings.

DETAILED DESCRIPTION OF ILLUSTRATED EMBODIMENTS

Figure 1:
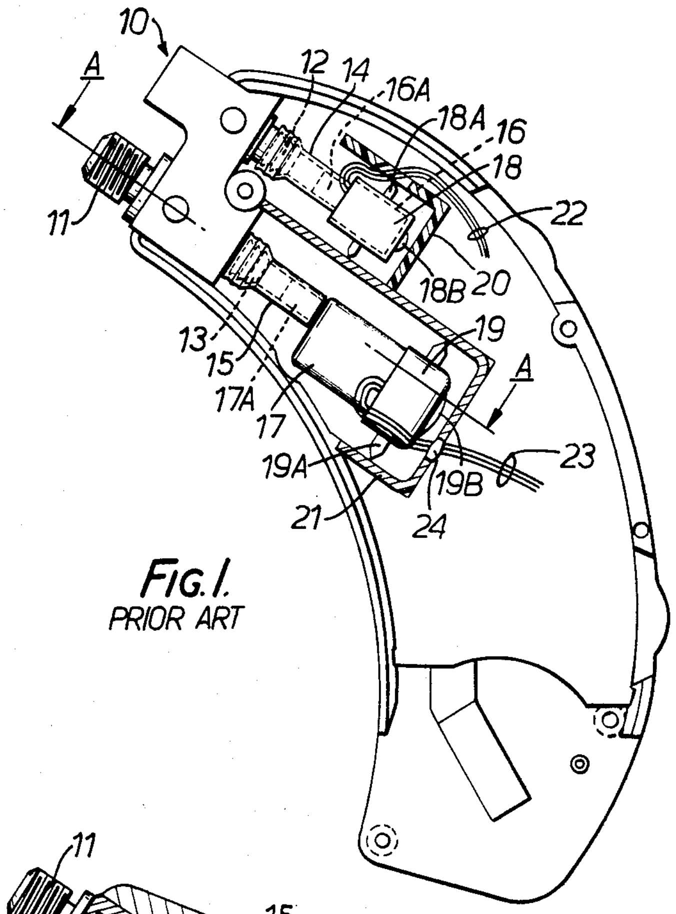
FIG. 1. PRIOR ART
FIG. 1 illustrates a conventional mounting arrangement for the transducers of a "behind the ear" type of hearing aid.

The hearing aid of FIG. 1 has an acoustical inlet port 10 and an acoustical outlet port 11. The outlet port 11 is normally connected by acoustical conducting tubing (not shown) to the ear of a user of the hearing aid. The inlet port 10 and outlet port 11 each terminate, within the housing of the hearing aid, in rigid tubes 12 and 13, respectively. The tubes 12 and 13 are connected, by short lengths of rubber tubing 14 and 15, respectively, to the microphone 16 and receiver 17. The short lengths of tubing 14 and 15 are each a tight fit over respective tubular projections 16A and 17A from the housings of the microphone 16 and the receiver 17. Projections 16A and 17A are acoustic conduits to, respectively, the input cavity of the microphone diaphragm and the output cavity of the receiver.

The diaphragm of the microphone 16 lies perpendicular to the plane of the paper and the diaphragm of the receiver 17 lies parallel to the plane of the paper on which FIG. 1 is drawn. Both diaphragms are parallel to the axis of tube 13, tubing 15 and tubular projection 17A.

The microphone 16 and the receiver 17 are mounted on respective supports by buffers which comprise rubber buckets 18 and 19, respectively. The buckets 18 and 19 are provided with a plurality of radially extending rubber spikes 18A and 19A, respectively, which serve to locate the buckets firmly within their respective supports 20 and 21. Projections 18B and 19B, from the bases of rubber buckets 18 and 19, may not always bear against the supports 20 and 21, but when they do, they transmit vibrational energy via the compression mode. The support 21 is a shaped wall that may be made of a plastics or a metal material. Support 20 is normally made from a rigid plastics material. The wires 22 and 23 from the microphone 16 and receiver 17 have to leave the top of the buckets 18 and 19, respectively, and be fed via suitable channels to the amplification and other circuitry of the hearing aid (not shown). If, as is the case of the wires 23 from receiver 17 of FIGS. 1 and 2, those wires have to pass through an aperture in a transducer support, then an acoustic seal 24 is required at the aperture in the support.

It will be apparent, therefore, that both the microphone 16 and the receiver 17 are mounted within the hearing aid housing by a respective two-component suspension comprising a rubber tube (14, 15), and a rubber bucket with spikes.

Figure 3:
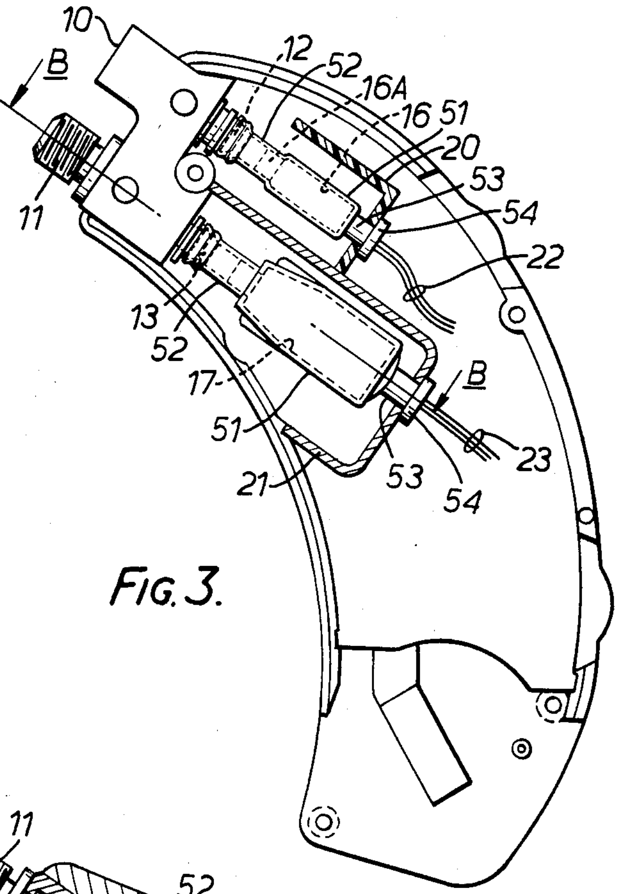
FIG. 3 depicts the hearing aid of FIG. 1, but with the present invention supporting the transducers.
Figure 4:
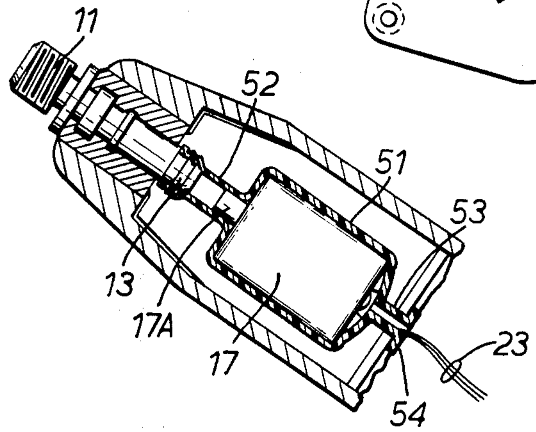
FIG. 4 is the view BB of FIG. 3, partly in section.
Figure 5:
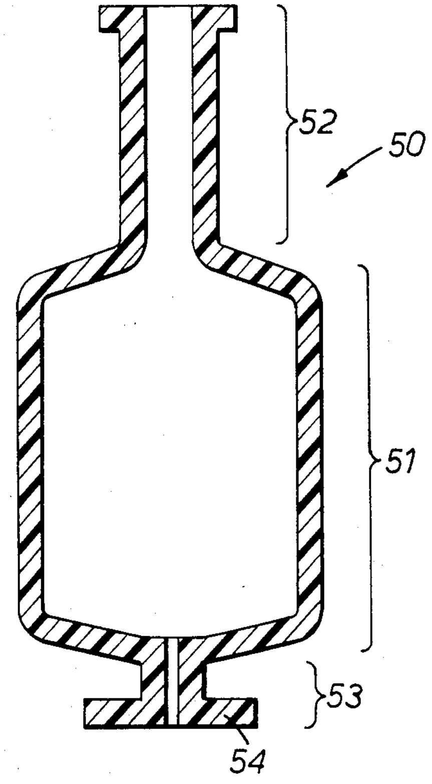
FIG. 5 is a sectional view of the present invention, as used in the hearing aid of FIG. 3.

With the present invention, as shown in FIGS. 3, 4 and 5, the transducers of the hearing aid are mounted with a single, moulded suspension 50 of soft rubber or similar resilient material. The suspension 50 has three major features. As shown in FIG. 5, the three major features are a transducer-supporting region 51 (which is adapted to be a close fit around, and almost encapsulate, a transducer), a tubular region 52 and a tubular foot 53.

Figure 2:
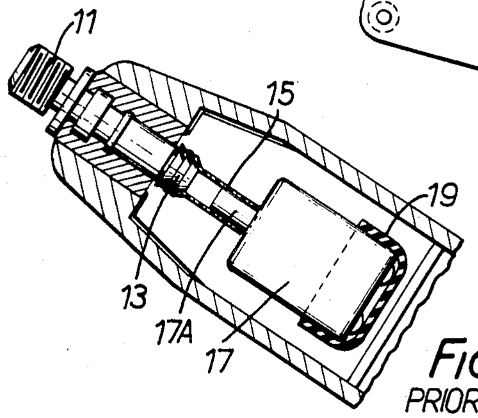
FIG. 2. PRIOR ART
FIG. 2 is the view AA of FIG. 1, partly in section.

As will be seen from FIGS. 3 and 4 (where the components of the hearing aid have been given the same reference numerals as they have in FIGS. 1 and 2), the tubular region 52 performs the same function as the tubes 14 and 15 of the arrangement shown in FIGS. 1 and 2. The flange 54 of tubular foot 53 passes through an aperture in the support for the transducers (as in the manner of one flange of a grommet) and secures the foot 53 relative to its associated support. Note the absence of the rubber spikes 18A and 19A from the present invention.

To fit the suspension of the present invention over a transducer, the transducer is first wired and the wiring passed through the central aperture in the tubular foot 53. The transducer is then inserted into the transducer supporting region 51. The moulding is then positioned around the transducers so that the tubular inlet 52 fits over the transducer tubular projection 16A (if the transducer is a microphone) or 17A (if the transducer is a receiver).

Those skilled in this art will recognise that the present invention has the following major benefits over the prior art:

(a) The mode of suspension is predominantly shear. This minimises the effect of the forces producing unwanted vibration of the transducer diaphragm and provides at least 10 dB more isolation than prior art suspensions made from the same material. It also provides a more precise placement of the transducer within the defined space for the transducer and releases more space within the hearing aid for other design purposes than the conventional suspension system.

(b) The effectiveness of the suspension is less critical of the compliance and damping properties of the material used in manufacture than in the prior art systems, a consequence of which is that the suspension of the present invention is easier to fabricate.

(c) The present invention provides for easy passage of electrical connections through the walls which surround the defined space. In some cases, such as in hearing aids, it is essential to acoustically isolate the transducer from transmission of air-borne sound. The suspension of the present invention provides access for wiring which is superior to existing designs (where the walls have to be breached for access purposes and the wires protected from damage as they pass through the walls by a protective sleeving, by a sealing compound or by both). A further advantage is that the wiring passageway in most applications does not have to be sealed as is required in existing designs to preserve the acoustical isolation integrity of the defined space.

Figure 6:
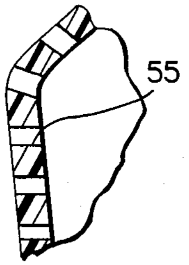
FIG. 6 is a partial cross-sectional view, in part similar to FIG. 5, showing another embodiment of the invention.
Figure 7:
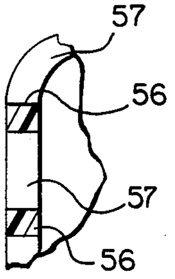
FIG. 7 is a partial cross-sectional view, in part similar to FIGS. 5 and 6, showing a still further embodiment of the invention.

It will also be apparent to those skilled in this art that modifications of the illustrated example of the present invention may be made without departing from the present inventive concept. For example, the embodiment of FIG. 5 shows the moulding as a continuous member, but in practice the region 51 may contain perforations 55 (FIG. 6) or may be formed in the manner of a web having intersections 56 and open areas 57 therebetween (FIG. 7), without affecting the suspension properties of the moulding.

Figure 8:
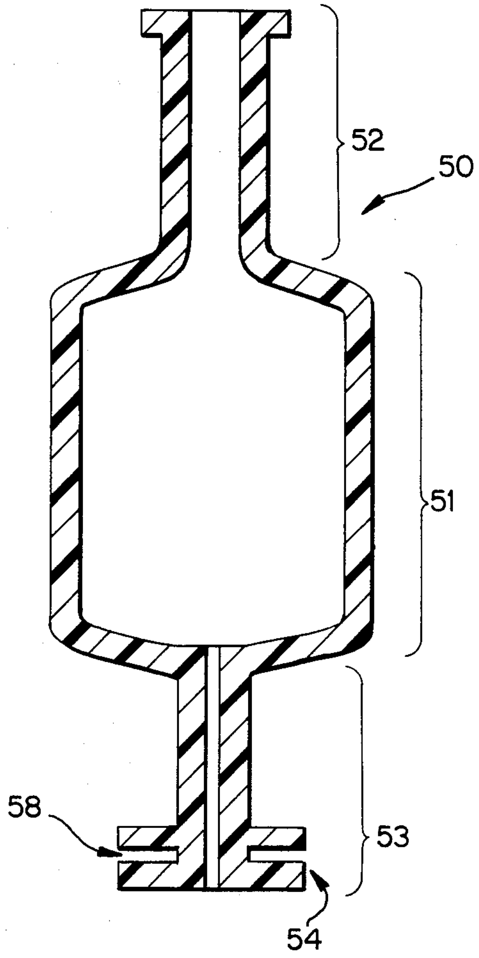
FIG. 8 is a cross-sectional view, in part similar to FIG. 5, showing yet another embodiment of the invention.

Furthermore, as shown in FIG. 8, the flange 54 may have an annular slot 58 formed in it, so that the mounting of the foot of the suspension 50 on a wall is effected with the wall projecting into the slot 58 and part of the flange 54 extending over each face of the wall in the region of the vicinity of the mounting aperture in the wall (that is, the mounting of the suspension is effected in precisely the way in which a grommet is fitted into an aperture). This variation of the embodiment featured as illustrated in FIG. 8 permits the suspension 50 to have a longer tubular foot 53, which is an advantageous feature in some electro-acoustic appliances.

We claim:

1. A mounting suspension for an electro-acoustical transducer to be supported in a predetermined location relative to an acoustic input or output of an appliance, said suspension comprising a moulding of elastomeric material, said moulding comprising:

(a) a transducer-supporting region having a shape which corresponds to the external shape of the transducer, said transducer-supporting region being adapted to be a tight fit around the transducer;

(b) a tubular region, extending from said transducer-supporting region, the end portion of said tubular region which is remote from the transducer-supporting region being close fitting over, and supportable by, the end region of a rigid tubular projection extending from the acoustic input or output of the appliance, said tubular region having an end portion closest to the transducer supporting region which is close fitting over said acoustical inlet or outlet tubular projection of the transducer when the transducer is located within the transducer-supporting region and the suspension is incorporated into the appliance; and (c) a tubular foot, extending from the end of the transducer-supporting region which is remote from said tubular region, said tubular foot including an annular flange extending radially from the axis of the tubular foot, said flange being adapted to retain the tubular foot in a position in which the tubular foot extends through a aperture formed in a mounting plate of the appliance.

2. A mounting suspension for an electro-acoustical transducer as defined in claim 1, in which said transducer-supporting region is perforated.

3. A mounting suspension for an electro-acoustical transducer as defined in claim 1, in which said transducer-supporting region is formed as a web.

4. A mounting suspension for an electro-acoustical transducer as defined in claim 1, in which said flange has an annular slot formed therein.

5. A mounting suspension for an electroacoustical transducer as defined in claim 2, in which said flange has an annular slot formed therein.

6. A mounting suspension for an electroacoustical transducer as defined in claim 3, in which said flange has an annular slot formed therein.

* * * * *